United States Patent [19]
Akiyama

[11] Patent Number: 4,540,281
[45] Date of Patent: Sep. 10, 1985

[54] DOUBLE-BEAM SPECTROPHOTOMETER

[75] Inventor: Osamu Akiyama, Kyoto, Japan

[73] Assignee: Shimadzu Corporation, Kyoto, Japan

[21] Appl. No.: 477,523

[22] Filed: Mar. 21, 1983

[30] Foreign Application Priority Data

Aug. 30, 1982 [JP] Japan .................................. 57-151046

[51] Int. Cl.³ .............................................. G01J 3/42
[52] U.S. Cl. ..................................... 356/325; 250/228; 356/236
[58] Field of Search ............... 356/319, 323, 325, 445, 356/446, 447, 448, 236; 250/228

[56] References Cited

U.S. PATENT DOCUMENTS

| | | | |
|---|---|---|---|
| 2,347,067 | 4/1944 | Shurcliff | 356/236 |
| 2,515,762 | 7/1950 | Dimmick | 356/236 X |
| 2,992,588 | 7/1961 | Henderson | 356/236 X |
| 4,455,097 | 6/1984 | Ichikawa et al. | 356/323 |

Primary Examiner—F. L. Evans
Attorney, Agent, or Firm—Fidelman, Wolffe and Waldron

[57] ABSTRACT

A double-beam spectrophotometer which uses an integrating sphere for measurement of the total reflected light from a sample or only the diffuse reflection component thereof. The sphere is provided with a first pair of windows in which a sample and a reference are detachably and exchangeably set and a second pair of windows through one of which one of a sample and a reference light beam enters the integrating sphere so as to impinge perpendicularly on said sample or reference set in one of said first pair of windows, while through the other of said second pair of windows the other of said sample and reference light beams enters said integrating sphere to impinge aslant on said reference or sample set in the other of said first pair of windows. The positions of said sample and reference are exchanged in accordance with the type of measurement to be made.

6 Claims, 8 Drawing Figures

PRIOR ART

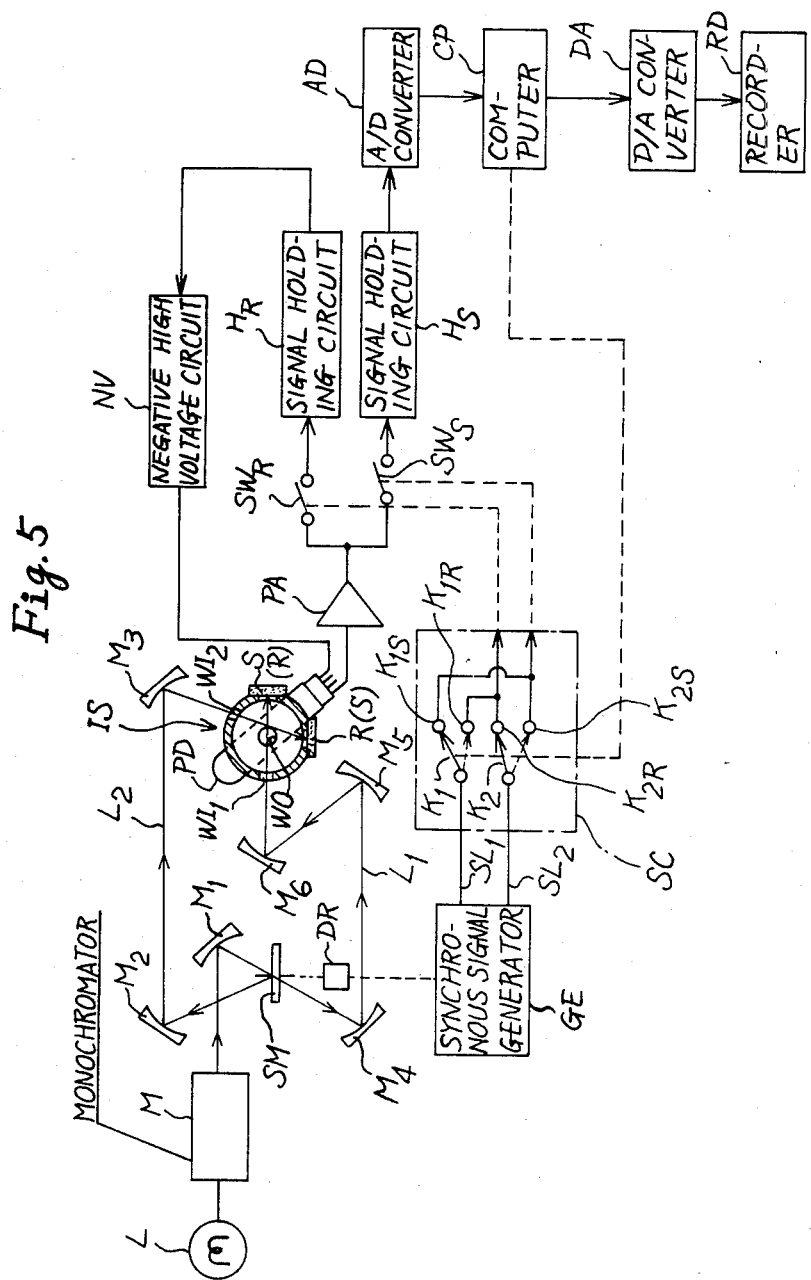

DOUBLE-BEAM SPECTROPHOTOMETER

BACKGROUND OF THE INVENTION

This invention relates to a double-beam spectrophotometer provided with an integrating sphere for measurement of the spectral reflection characteristics of a sample.

Generally, the reflection of light from the surface of an object comprises diffuse reflection and specular reflection, so that the light reflected from the surface is a mixture of both diffusely reflected and specularly reflected components.

There are two methods of measuring the light reflected from the surface of an object by using an integrating sphere.

One is to measure the diffuse reflection component only and the other is to measure the total reflected light including both the diffuse reflection component and the specular reflection component.

When the above two methods of measurement are conducted by using conventional double-beam spectrophotometers provided with a single integrating sphere, various difficulties are encountered.

One conventional spectrophotometer is provided with an integrating sphere such as shown at IS in FIG. 1. The sphere IS is formed with a pair of inlet windows $WI_R$ and $WI_S$, through which a reference light beam $L_R$ and a sample light beam $L_S$ parallel with each other are introduced into the integrating sphere IS. The integrating sphere is also formed with an outlet window WO, outside which a photodetector not shown is arranged to receive the light from inside the integrating sphere. In the sphere there are a sample to be measured (which will be referred to merely as the sample and designated by S) and a sample to be used as the reference or standard (which will be referred to merely as the reference and designated by R) so arranged that their respective surfaces face inwardly of the integrating sphere and are inclined relative to the sample and reference beams $L_S$ and $L_R$ respectively so that the specular reflection components of the two incident light beams reflected from the reference and sample surfaces hits a particular area on the interior surface of the integrating sphere.

When only the diffuse reflection component of the light incident on the sample S is to be measured, the specular reflection component thereof is removed by a light trap TR located in the above-mentioned particular area of the interior surface of the integrating sphere. When the total reflected light including the diffuse reflection and specular reflection components is to be measured, the light trap TR is replaced by a diffusely reflecting white plate PL.

The above-mentioned conventional arrangement, however, has the following defects: Firstly, since the surfaces of the sample and the reference facing inwardly of the integrating sphere IS are not tangential to the sphere, the interior surface of the sphere is not completely spherical so that complete integration cannot be attained. Secondly, in order to conduct two different kinds of measurement, a light trap and a white plate must alternatively be used, so that the operator of the instrument may make a mistake in exchanging the two members. Thirdly, it is practically quite difficult that the interior surface of the integrating sphere and that of the white plate should continuously have substantially the same characteristic with respect to reflection of light as time passes, so that errors are likely to be introduced into the results of measurement.

Another conventional spectrophotometer is provided with a single integrating sphere as shown in FIGS. 2a and 2b, wherein the same reference symbols as in FIG. 1 designate corresponding parts or elements, so that no explanation will be given to them. When the diffuse reflection component only is to be measured, both the sample S and the reference R are so mounted on the integrating sphere IS that the sample and reference beams $L_S$ and $L_R$ introduced into the sphere through the respective inlet windows $WI_S$ and $WI_R$ impinge on the inner surfaces of the sample and the reference perpendicularly thereto so that the specular reflection components from both the surfaces go out of the integrating sphere through the inlet windows.

When the total quantity of the reflected light including both the diffuse reflection component and the specular reflection component is to be measured, a spacer SP is interposed between the sample S and the integrating sphere IS thereby to set the sample S aslant relative to the sphere, so that the specular reflection component of the light reflected from the sample hits the inner surface of the integrating sphere so as not to come out therefrom.

The arrangement, however, has the following defects: Firstly, with the spacer SP interposed between the sample and the integrating sphere, the sample is set aslant and positioned outwardly of a plane tangential to the integrating sphere, so that a portion of the diffuse reflection component of the light reflected from the sample hits the spacer, thereby to prevent correct measurement by the integrating sphere. Secondly, the spacer must be attached to or detached from the integrating sphere, depending upon the kind of measurement to be made. The operation is certainly troublesome.

SUMMARY OF THE INVENTION

Accordingly, the object of this invention is to provide a double-beam spectrophotometer having a single integrating sphere which eliminates the above-mentioned and other defects of the conventional spectrophotometers of this type.

The spectrophotometer constructed in accordance with this invention is provided with an integrating sphere formed with a first pair of windows in which a sample and a reference are set so as to be tangential to the integrating sphere and a second pair of windows through which the sample beam and the reference beam are introduced into the integrating sphere so as to impinge on the sample and the reference, respectively, set in the first pair of windows.

In a preferred embodiment of the invention, one of the first pair of windows and the corresponding one of the second pair of windows are so arranged that a straight line connecting the center of the former one window and that of the latter corresponding one window does not pass the center of the integrating sphere. With this off-center arrangement, the light beam introduced into the integrating sphere through the latter one window impinges aslant on the sample or reference set in the former one window.

The sample and the reference set in the first pair of windows are exchanged in accordance with the kind of measurement. In other words, the positions of the sample and the reference mounted on the integrating sphere when only the diffuse reflection component of the light reflected from the sample is to be measured are exchanged when the total reflection light including both the diffuse reflection component and the specular reflection component is to be measured.

BRIEF DESCRIPTION OF THE DRAWING

FIG. 4b is a view similar to FIG. 3b but showing the integrating sphere of FIG. 4a; and FIG. 5 is a schematic diagram of a double-beam spectrophotometer constructed in accordance with the invention with the integrating sphere shown in FIGS. 3a and 3b.

DETAILED DESCRIPTION OF THE ILLUSTRATED EMBODIMENTS

Figure 1:
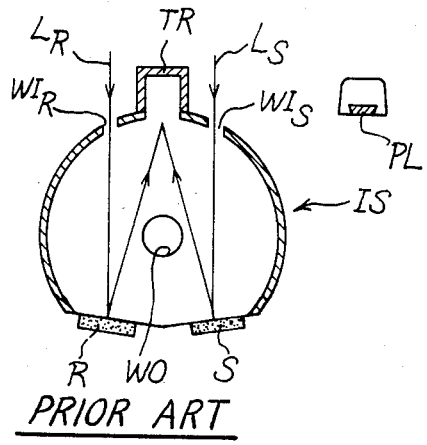
FIG. 1 is a schematic sectional view of a conventional integrating sphere used in a double-beam spectrophotometer.
Figure 2A:
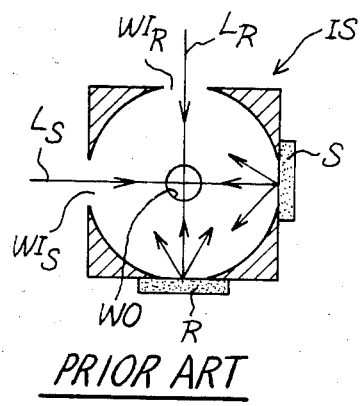
FIG. 2a is a schematic sectional view of another conventional integrating sphere when it is used for measurement of only the diffuse reflection component of the light reflected from a sample.
Figure 2B:
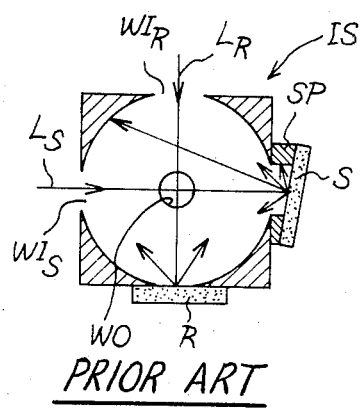
FIG. 2b is a schematic sectional view of the integrating sphere of FIG. 2a when it is used for measurement of both the diffuse reflection component and the specular reflection component of the light reflected from a sample.
Figure 3A:
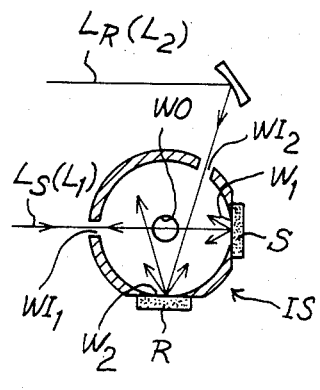
FIG. 3a is a schematic sectional view of an integrating sphere constructed in accordance with the invention when it is used for measurement of only the diffuse reflection component of the light reflected from a sample.

Referring to FIG. 3a, there is shown an integrating sphere IS constructed in accordance with one embodiment of the invention. The sphere IS is provided with a window $W_1$ in which a sample S is detachably fitted, and a window $W_2$ in which a reference R is detachably fitted. On the side diametrically opposite to the window $W_1$ there is formed in the sphere an inlet window $WI_1$ through which a sample light beam $L_S$ is introduced into the integrating sphere so as to impinge on the inner surface of the sample S set in the window $W_1$ perpendicularly thereto.

The specular reflection component of the light reflected from the sample S goes out through the window $WI_1$ so as not to be detected.

Laterally displaced or offset from the point diametrically opposite to the window $W_2$ there is formed in the sphere IS another inlet window $WI_2$ through which a reference light beam $L_R$ is introduced into the sphere so as to impinge aslant on the reference R set in the window $W_2$. If the light reflected from the surface of the reference R contains a specular reflection component, it is impossible to remove the component. However, the reference R is provided in order to obtain a signal for correcting the baseline of the signal obtained from measurement of the sample S. To this end the reference R has only to respond to the wavelength characteristics of the light source and the drift of the measuring electrical circuit. Therefore, it is not necessary to eliminate the specular reflection component of the reflected light from the reference R. The sphere IS is further provided with an outlet window WO outside which a photodetector not shown is located so as to receive the light emanating from inside the sphere.

Figure 3B:
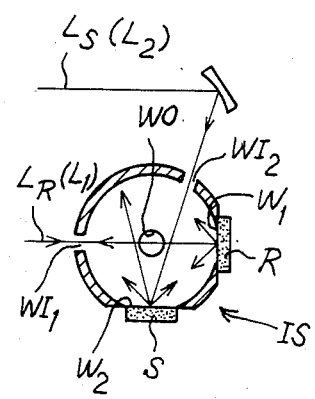
FIG. 3b is a schematic sectional view of the integrating sphere of FIG. 3a when it is used for measurement of both the diffuse reflection component and the specular reflection component of the light reflected from a sample.

In FIG. 3b the positions of the reference R and the sample S in FIG. 3a are exchanged, so that the sample S is set in the window $W_2$ while the reference R is set in the window $W_1$. With this arrangement the sample beam $L_S$ is introduced into the integrating sphere IS through the inlet window $WI_2$ so as to impinge aslant on the sample S, so that the specular reflection component of the light reflected from the sample hits the interior surface of the integrating sphere. This means that the total reflected light from the sample including both the diffuse reflection component and the specular reflection component is measured.

In FIG. 3b, the reference beam $L_R$ is incident on the reference R perpendicularly thereto, so that the specular reflection component of the light reflected from the reference R goes out through the inlet window $WI_1$. For the same reason as mentioned above, this exercises no adverse influence on the baseline correction.

Referring now to FIG. 5 there is schematically shown a double-beam spectrophotometer provided with the integrating sphere IS shown in FIGS. 3a and 3b. A light source L radiates a light over a range of measuring wavelengths. A monochromator M receives the light from the light source L and generates a monochromatic light of a selected wavelength. The monochromatic light is reflected by a mirror $M_1$ toward a beam splitter comprising a rotatable sector mirror SM which functions as a chopper. The sector mirror SM is driven by a suitable drive DR.

As the sector mirror SM is rotated, it causes the monochromatic light from the monochromator M to advance alternately along a first and a second optical path. The first optical path and the light beam thereon will be commonly designated by $L_1$ while the second optical path and the light beam thereon will be commonly designated by $L_2$.

The light $L_1$ passing the sector mirror SM is reflected by mirrors $M_4$, $M_5$ and $M_6$ so as to enter the integrating sphere IS through the inlet window $WI_1$. The light $L_2$ reflected by the sector mirror SM is further reflected by mirrors $M_2$ and $M_3$ so as to enter the integrating sphere IS through the inlet window $WI_2$ alternately with the light beam $L_1$ entering the sphere through the other inlet window $WI_1$.

A photodetector PD is located so as to cover the window WO of the integrating sphere IS and receive the light emerging from the sphere through the window WO. The photodetector PD can, for example, be a photomultiplier tube, the output of which is applied to a preamplifier PA. The output signal of the preamplifier is in its turn applied through a parallel pair of sampling switches $SW_R$ and $SW_S$ to a parallel pair of signal holding circuits $H_R$ and $H_S$.

The output of the signal holding circuit $H_R$ is fed back to the photodetector PD through a negative high voltage circuit NV so as to adjust the sensitivity of the photodetector PD thereby to keep constant the output signal of the photodetector caused by the reference beam. The output of the signal holding circuit $H_S$ corresponds to the output signal of the photodetector PD caused by the reflected light from the sample under measurement and is applied through an analog-to-digital converter AD to a computer CP, the output of which is applied through a digital-to-analog converter DA to a recorder RD so as to be recorded therein.

As previously mentioned, the positions of the reference R and the sample S set on the integrating sphere IS are exchanged in accordance with the kind of measurement to be made, that is, whether the total reflected light from the sample or only the diffuse reflection component thereof is to be measured, and which of the beams on the first and the second optical paths $L_1$ and $L_2$ becomes the reference or the sample beam is determined in accordance with the positions of the sample and the reference on the integrating sphere. It is required that regardless of which of the reference and sample beams advances along which of the first and second optical paths, the output signal of the photodetector PD caused by the reference beam should always be applied to the signal holding circuit $H_R$ while the output signal of the photodetector PD caused by the sample beam should always be applied to the signal holding circuit $H_S$.

To satisfy the above requirement, a switch controller SC operates in response to a synchronous signal generator GE to effect alternate opening and closing of the sampling switches $SW_R$ and $SW_S$ in the following manner.

Suppose that the sample S and the reference R are set in the windows $W_1$ and $W_2$, respectively, of the integrating sphere IS as shown in FIG. 3a to measure only the diffuse reflection component of the reflected light from the sample, so that the light beams on the first and second optical paths $L_1$ and $L_2$ are the sample and reference beams, respectively.

The signal generator GE operates in synchronism with the rotation of the sector mirror SM to generate alternately a first signal $SL_1$ while the sector mirror SM allows the sample beam on the first path $L_1$ to enter the integrating sphere IS to hit the sample S therein and a second signal $SL_2$ while the sector mirror SM allows the reference beam on the second optical path $L_2$ to enter the sphere IS to hit the reference R therein.

The switch controller SC includes a pair of switches $K_1$ and $K_2$ each having a pair of stationary contacts $K_{1R}$ and $K_{1S}$, and $K_{2R}$ and $K_{2S}$. In accordance with the positions of the sample S and the reference R set on the integrating sphere, the computer CP determines at which of the stationary contacts each of the switches $K_1$ and $K_2$ should be closed, and under the present condition that the sample S and reference R are set in the windows $W_1$ and $W_2$ respectively as shown in FIG. 3a, the switches $K_1$ and $K_2$ are kept closed at $K_{1S}$ and $K_{2R}$ respectively. Therefore, the control signal $SL_1$ generated while the sample beam $L_1$ is impinging on the sample S causes the sampling switch $SW_S$ to be closed, with the other sampling switch $SW_R$ being kept open at this time, so that the output signal of the photodetector PD caused by the sample beam $L_1$ is applied through the closed switch $SW_S$ to the signal holding circuit $H_S$, and the control signal $SL_2$ generated alternately with the signal $SL_1$ while the reference beam $L_2$ is impinging on the reference R causes the sampling switch $SW_R$ to be closed, with the other sampling switch $SW_S$ having been opened at this time, so that the output signal of the photodetector PD caused by the reference beam $L_2$ is applied through the closed switch $SW_R$ in the signal holding circuit $H_R$.

When the total reflected light from the sample is to be measured, the positions of the sample S and the reference R in FIG. 3a are exchanged so that the sample S and the reference R are set in the windows $W_2$ and $W_1$, respectively, as shown in FIG. 3b. The computer then causes the switches $K_1$ and $K_2$ to be closed at the opposite sides $K_{1R}$ and $K_{2S}$ respectively as shown in phantom. In this case, the beams on the first and second optical paths $L_1$ and $L_2$ become the reference and sample beams respectively. Therefore, the control signal $SL_1$ generated while the reference beam $L_1$ is impinging on the reference R causes the sampling switch $SW_R$ to be closed, with the other sampling switch $SW_S$ being opened at this time, and the control signal $SL_2$ generated alternately with the control signal $SL_1$ while the sample beam $L_2$ is impinging on the sample S causes the sampling switch $SW_S$ to be closed, with the other sampling switch $SW_R$ having been opened at this time.

Figure 4A:
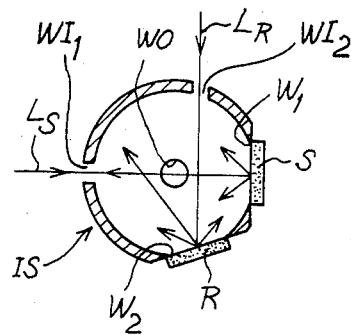
FIG. 4a is a view similar to FIG. 3a but showing a modified form of the integrating sphere.
Figure 4B:
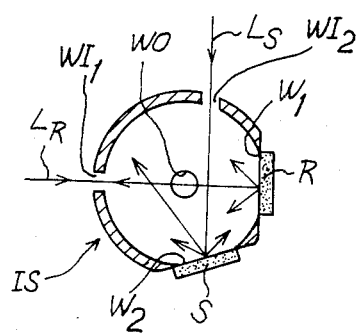

A modified form of the integrating sphere of FIGS. 3a and 3b is shown in FIGS. 4a and 4b, wherein the same reference symbols as in FIGS. 3a and 3b designate corresponding parts.

In FIGS. 4a and 4b the two beams $L_R$ and $L_S$ enter the integrating sphere IS so that they intersect perpendicularly to each other, and the windows $W_1$ and $W_2$ in which the sample S and the reference R are set are so arranged that the plane of one of the windows, say, $W_1$ is perpendicular to the light beam incident thereon while the plane of the other window $W_2$ is inclined or aslant relative to the light beam incident thereon.

When only the diffuse reflection component of the light reflected from a sample S is to be measured, the sample is set in the window $W_1$, with a reference R being set in the other window $W_2$ as shown in FIG. 4a. When the total reflected light from the sample including the diffuse reflection and specular reflection components is to be measured, the sample S is set in the window $W_2$, with the reference R being set in the window $W_1$ as shown in FIG. 4b.

The integrating sphere IS of FIGS. 4a and 4b may be used in the system of FIG. 5 in the same manner as previously mentioned.

In the system of FIG. 5 the reference and sample light beams are introduced into the integrating sphere through the inlet windows, with the photodetector being located adjacent the outlet window WO. It is possible to exchange the positions of the light source and the photodetector so that the light from the source is introduced into the integrating sphere through the single window WO and the sample and reference light beams are taken out of the sphere through the windows $WI_1$ and $WI_2$. The arrangement is useful for measurement of fluorescent materials or for elimination of the adverse influence of the radiation from a heated sample when near-infrared light is used for measurement.

As is apparent from the foregoing description, the present invention is based on the idea that the output signal obtained by measurement of the reference must be responsive only to fluctuation of the light source or drift of the measuring electrical circuits and it does not matter whether the light beam impinges on the reference perpendicularly or aslant thereto, or whether the specular reflection component of the reflected light from the reference is eliminated or not. Thus the integrating sphere of the invention is provided with a pair of windows for having a sample or a reference fitted therein, and the sample or reference beam is incident perpendicularly on the plane of one of the windows and aslant on the plane of the other of the windows. The positions of the sample and the reference set in the two windows are exchanged in accordance with the type of measurement to be conducted.

With this arrangement of the invention it has become unnecessary to exchange a light trap and a white plate, or attach a spacer to and detach it from the integrating sphere as in the prior art devices. Also the invention has solved the problem that the optical characteristic of the white plate changes as time passes and the problem that the spacer is likely to cut off a portion of the diffuse reflection component of the reflected light from the sample under measurement. Advantageously, it is possible to arrange both the sample and the reference materials close to the inner surface of the integrating sphere.

In the above description, the total reflected light from the sample always contains both the diffuse reflection and specular reflection components. If the sample is like an evaporated mirror the reflected light from which contains little or no diffuse reflection component, it is possible to measure the specular reflection of the sample by measuring the total reflected light therefrom.

What I claim is:

1. A double-beam spectrophotometer comprising:
means for providing a first and a second light beam; an integrating sphere provided with a first pair of windows in which a sample and a reference are detachably and exchangeably set and a second pair of windows so arranged relative to said first pair of windows that one of said first and second light beam entering said integrating sphere through one of said second pair of windows impinges perpendicularly on one of said sample and reference set in the corresponding one of said first pair of windows while the other of said first and second light beams entering said integrating sphere through the other of said second pair of windows impinges aslant on the other of said reference and sample set in the other of said first pair of windows; and means for measuring the light emerging from said integrating sphere and wherein one of said second pair of windows of said integrating sphere is arranged at a position diametrically opposite to one of said first pair of windows while the other of said second pair of windows is laterally displaced from the position diametrically opposite to the other of said first pair of windows.

2. The double-beam spectrophotometer of claim 1, wherein said light beam providing means comprises means for providing a monochromatic light beam and a beam splitter for splitting said monochromatic light beam into said first and said second light beams, and wherein said measuring means comprises a photodetector for receiving the light emerging from said integrating sphere to produce a corresponding output signal, a feedback circuit connected to said photodetector, signal processing means connected to said photodetector, and switching means operable in association with said beam splitter to apply to said signal processing means said output signal from said photodetector caused by the light from said integrating sphere while one of said first and second light beams is impinging on said sample and alternately to said feedback circuit said output signal from said photodetector caused by the light from said integrating sphere while the other of said first and second light beams is impinging on said reference whereby the sensitivity of said photodetector is kept constant.

3. The double-beam spectrophotometer of claim 1, wherein said first and second light beams cross perpendicularly to each other in said integrating sphere and one of said first pair of windows of said integrating sphere is so arranged that one of said first and second light beams impinges perpendicularly on one of said sample and reference set in said one window while the other of said first pair of windows is so arranged that the other of said first and second light beams impinges aslant on the other of said reference and sample set in said other window.

4. A double-beam spectrophotometer comprising a light source for radiating a light over a range of measuring wavelengths; a monochromator receiving said light to generate a monochromatic light of a selected wavelength; a beam splitter for splitting said monochromatic light alternately into a first and a second light beam; an integrating sphere; optical means for directing said first and second light beams to enter said integrating sphere; said integrating sphere being provided with a first pair of windows in which a sample and a reference are detachably and exchangeably set and a second pair of windows one of which is arranged at a position diametrically opposite to one of said first pair of windows while the other of said second pair of windows is laterally displaced from the position diametrically opposite to the other of said first pair of windows so that one of said first and second light beams entering said integrating sphere through said one of said second pair of windows impinges perpendicularly on one of said sample and reference set in the corresponding one of said first pair of windows while the other of said first and second light beams entering said integrating sphere through said other of said second pair of windows impinges aslant on the other of said reference and sample set in the other of said first pair of windows; a photodetector for receiving the light emerging from said integrating sphere to generate a corresponding output signal; a feedback circuit connected to said photodetector; signal processing means connected to said photodetector; and switching means operable in association with said beam splitter to apply to said signal processing means said output signal from said photodetector caused by the light from said integrating sphere while one of said first and second light beams is impinging on said sample and alternately to said feedback circuit said output signal from said photodetector caused by the light from said integrating sphere while the other of said first and second light beams is impinging on said reference whereby the sensitivity of said photodetector is kept constant.

5. An integrating sphere for use in a double-beam spectrophotometer comprising a wall for defining a spherical space, a first pair of windows in which a sample and a reference are detachably and exchangeably set and a second pair of windows so arranged relative to said first pair of windows that a first light beam entering said spherical space through one of said second pair of windows impinges perpendicularly on one of said sample and reference set in the corresponding one of said first pair of windows while a second light beam entering said integrating sphere through the other of said second pair of windows impinges aslant on the other of said reference and sample set in the other of said first pair of windows and wherein one of said second pair of windows is arranged at a position diametrically opposite to one of said first pair of windows while the other of said second pair of windows is laterally displaced from the position diametrically opposite to the other of said first pair of windows.

6. The integrating sphere of claim 5, wherein said first and second light beams cross perpendicularly to each other in said spherical space and one of said first pair of windows is so arranged that one of said first and second light beams impinges perpendicularly on said sample or reference set in said one window while the other of said first pair of windows is so arranged that the other of said first and second light beams impinges aslant on said reference or sample set in said other window.

* * * * *